United States Patent [19]

Brox

[11] Patent Number: 4,744,988
[45] Date of Patent: May 17, 1988

[54] SOFT GELATIN CAPSULES AND METHODS FOR THEIR PRODUCTION

[75] Inventor: Werner Brox, Beerfelden, Fed. Rep. of Germany

[73] Assignee: R. P. Scherer Corporation, Troy, Mich.

[21] Appl. No.: 943,386

[22] Filed: Dec. 17, 1986

Related U.S. Application Data

[63] Continuation of Ser. No. 667,006, Oct. 31, 1984.

[30] Foreign Application Priority Data

Mar. 2, 1983 [DE] Fed. Rep. of Germany ....... 3307353

[51] Int. Cl.$^4$ .............................................. A61K 9/48
[52] U.S. Cl. ...................................... 424/456; 426/3; 426/5; 428/402.2
[58] Field of Search ..................... 428/402.2; 426/3, 5; 424/456

[56] References Cited

U.S. PATENT DOCUMENTS

| | | | |
|---|---|---|---|
| 2,172,357 | 9/1939 | Brown | 252/194 |
| 2,847,346 | 8/1958 | Vaughan | 424/456 |
| 2,870,060 | 1/1959 | Bryan | 424/456 |
| 2,870,062 | 1/1959 | Stanley et al. | 514/774 |
| 2,889,252 | 6/1959 | Valentine et al. | 424/456 |
| 3,520,971 | 7/1970 | Benford | 424/456 |
| 3,653,934 | 4/1972 | Rolle | 514/962 |
| 3,656,997 | 4/1972 | Cordes | 424/456 |
| 3,779,942 | 12/1973 | Bolles | 424/456 |
| 3,784,684 | 1/1974 | Bossert et al. | 424/456 |
| 4,002,718 | 1/1977 | Gardella et al. | 424/456 |
| 4,088,750 | 5/1978 | Cresswell et al. | 424/456 |
| 4,198,391 | 4/1980 | Grainger | 424/456 |
| 4,366,145 | 12/1982 | Stoopak et al. | 424/456 |
| 4,428,927 | 1/1984 | Ebert et al. | 424/456 |

FOREIGN PATENT DOCUMENTS

| | | |
|---|---|---|
| 1617629 | 3/1971 | Fed. Rep. of Germany . |
| 2209526 | 9/1973 | Fed. Rep. of Germany . |
| 2546371 | 4/1977 | Fed. Rep. of Germany . |
| 715879 | 9/1954 | United Kingdom . |
| 1135709 | 12/1968 | United Kingdom . |

OTHER PUBLICATIONS

Khawam et al., "Uber den Einfluss Nichtionogener Losungsvermittler auf die Loslichkeit von Sulfanilamid," Sci. Pharm., 33 (1965), 2, pp. 90–101.

Johnson et al., "The Comparability of Dosage Regimens of Lanoxin Tablets and Lanoxicaps, " British Journal of Clinical Pharmacology, 4, pp. 209–211 (1977).

Czetsch-Lindenwald et al., *Arzneikapseln* (Aulendorf, 1962), pp. 26–27.

Voight, *Lehrbuch der Pharmaseutischen Technologie* (3rd ed., 1979), pp. 244–245.

Fiedler, *Lexikon Der Hilfsstoffe fur Pharmazie, Kosmetik und angrenzende Gebiete* (Aulendorf, 1981), pp. 846–847.

Ebert, "Soft Elastic Gelatin Capsules: A Unique Dosage Form," Pharmaceutical Technology (Oct., 1977).

*Primary Examiner*—Ronald W. Griffin
*Attorney, Agent, or Firm*—Allegretti, Newitt, Witcoff & McAndrews

[57] ABSTRACT

A soft gelatin capsule comprising a shell of gelatin and a softener, and a filling consisting of a polyethylene glycol and a low polyhydric alcohol and at least one active substance, characterized in that (a) the dried shell of the capsule contains 4 to 40% by weight of sorbital or sorbitanes;

(b) at least 50% by weight of the polyethylene glycol used in the filling for dissolving or suspending the active substance is a polyethylene glycol having a mean molecular weight of 600; and (c) the capsule filling comprises up to 20% by weight of glycerol and/or 1,2-propylene glycol.

5 Claims, 1 Drawing Sheet

SOFT GELATIN CAPSULES AND METHODS FOR THEIR PRODUCTION

This is a continuation of copending application Ser. No. 667,006, filed Oct. 31, 1984.

BACKGROUND OF THE INVENTION

Field of the Invention and Description of the Prior Art

This invention relates to improved forms of medicine, more particularly to soft gelatin capsules containing polyethylene glycol which distinguish themselves by an exceptionally high physical stability and durability.

After a method for the production of soft gelatin capsules had been found in the thirties by which a capsule can be produced and filled in a single operation, gelatin capsules, and in particular soft gelatin capsules, gained more and more importance as a form of medicine. They present a number of advantages over other forms of administration. They are, for instance, odorless and tasteless, easy to swallow, and their swelling properties and solubility in water ensure that the active substances are easily released in the stomach. There are quite a number of active substances which because of their sensitivity to oxidation and light, their thermal instability, or their hygroscopicity cannot be processed into other forms of medicines, but which can be enclosed in capsules without their efficiency being impaired.

Soft gelatin capsules are predominantly employed for enclosing liquids, more particularly oily solutions, suspensions or emulsions. Filling materials normally used are vegetable, animal or mineral oils, liquid hydrocarbons, volatile oils and polyethylene glycols. To improve the consistency, fats or waxes are used or added.

As compared with the other possible filling materials for soft gelatin capsules, polyethylene glycols offer a number of particularities. Contrary to oily liquids, liquid polyethylene glycols can be mixed with water without limitation, and the solid polyethylene glycols are also well soluble in water. Since on the other hand polyethylene glycols are at the same time capable of solving many active substances which themselves are not or only difficulty soluble in water, the use of polyethylene glycols enables such active substances to be released in a particularly favorable manner. Active substances which are difficulty soluble in water and which are dissolved or suspended in polyethylene glycols and then filled into soft gelatin capsules, distinguish themselves in many cases by an exceptionally high bio-availability of the active substances. In Br. J. Clin. Pharmac. (1977), 4, pages 209 to 211, for instance, it has been reported that an especially good bio-availability of digoxin is obtained when the active substance is administered in the form of a polyethylene glycol solution enclosed in a soft gelatin capsule.

In spite of these, mainly bio-pharmaceutical, advantages of soft gelatin capsules the fillings of which contain polyethylene glycols, very considerable difficulties are encountered in the production of physically stable and durable capsules.

Polyethylene glycol has a high affinity to both the material of the gelatin capsule and the softeners used in the shell. The softener normally used for gelatin capsules containing the usual filling materials is in the first line glycerol, but sorbitol and, to a limited degree, polyethylene glycols themselves have also been known as softeners (compare Czetach-Lindenwald and Fahrig, Medicine Capsules, Aulendorf, 1962, pages 26/27, or R. Voight, Manual of Pharmaceutical Technology, 3rd edition, 1979, page 244). It has been generally assumed that the higher hygroscopicity of glycerol renders it more efficient as a softener than sorbitol, and accordingly glycerol is employed in most cases (compare also German Patent Specification No. 22 09 526). However, in most of the cases, the hardness and flexibility of the shells of the capsules start to change shortly after the production of such capsules, due to the reciprocal effects between the fillings, which contain polyethylene glycols, and the soft gelatin capsules, which contain softeners. In many cases, the shells of the capsules get so brittle that the enclosures burst and the fillings contained in them are set free. Sometimes it even happens that such brittle capsules are destroyed already during transportation as bulk material because they cannot resist the mechanical stresses encountered.

In other cases, the affinity of polyethylene glycols to the shells may induce the polyethylene glycols to diffuse during storage from the fillings into the gelatin enclosure. Since the polyethylene glycols act as softeners, the capsules get very soft. They stick together and deform, and when sealed into plastic films they can no longer be pressed out without damage to the capsules. In many cases, the polyethylene glycol diffuses through the enclosure so that the surface of the shell gets smeary. Capsules in this condition must be regarded as bad.

German Patent Specification No. 22 09 526 describes soft gelatin capsules, the shell of which contains glycerol as a softener and the fillings of which contain polyethylene glycols with a mean molecular weight of between 300 to 600, together with a small proportion of glycerol and water. The polyethylene glycol for the capsules actually described in this Patent Specification consists exclusively of polyethylene glycol 400. German Patent Specification No. 22 09 526 states that optimum results are achieved with capsules of the described composition. However, if one tries to transfer the compositions specified in the said German Patent Specification No. 22 09 526 to capsules containing other active substances or of other capsule sizes, failures will be encountered, again and again, insofar as during storage, the capsules will change in hardness and flexibility, get brittle or soft, or polyethylene glycol will diffuse through the shell. And even when producing capsules in accordance with German Patent Specification No. 22 09 526, using the active substance specified therein, it will be found that the hardness of the capsules will change heavily during storage. So, there is still a need for soft capsules containing polyethylene glycol which can be manufactured in a reproducible manner as stable and durable medicines.

SUMMARY OF THE INVENTION

Accordingly, it is an object of the present invention to provide soft capsules containing polyethylene glycol and a method for producing the same in which the kinds and quantities of the filling materials used in addition to various selective active substances, on the one hand, and the capsule shells, on the other hand, are so adapted to each other that soft gelatin capsules, with solutions or suspensions containing polyethylene glycol are obtained in which the optimum hardness and flexibility, adjusted after production of the capsules, remains unchanged during storage and in which no polyethylene glycol diffuses through the capsule shell to render the polyethylene glycol smeary. This problem is solved by the soft gelatin capsule and a method for producing the same described in the claims.

After lengthy investigations and variations of a large number of conventional materials, namely different polyethylene glycols, different additives added to the said polyethylene glycols, different softeners and quantity ratios it was surprisingly found that the combination of features specified herein ensures that the soft gelatin capsules do not change in hardness during their storage between their production and their consumption by the patients and that no polyethylene glycols whatever diffuse through the enclosure of the capsule.

BRIEF DESCRIPTION OF DRAWINGS

The background of the invention and its departure from the art will be further described hereinbelow with reference to the accompanying drawings, wherein.

DETAILED DESCRIPTION OF THE PREFERRED EMBODIMENTS

Figure 1:
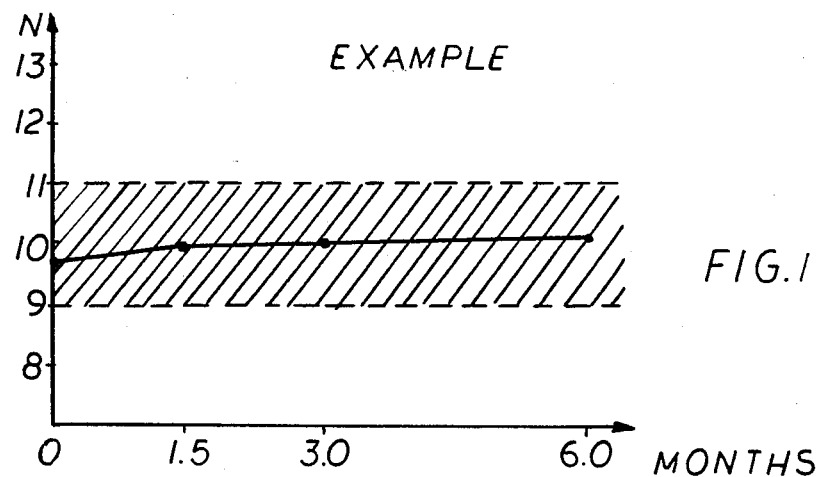
FIG. 1 is the example according to the invention which demonstrates a constant, optimum capsule hardness (N) after storage where capsules contain polyethylene glycol 600 in the filling and sorbitol and sorbitane in the shell.
Figure 2:
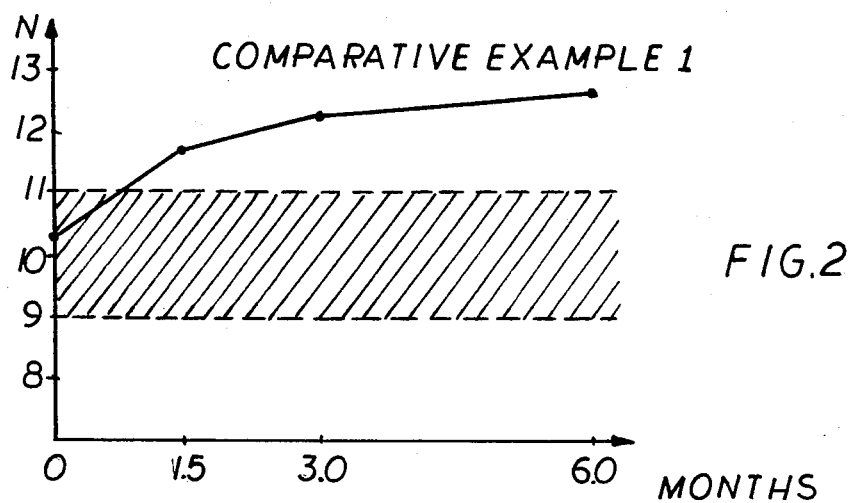
FIG. 2 is the Comparative Example 1 showing a very rapid increase in capsule hardness (N) after storage where capsules contain polyethylene glycol 600 in the filling and do not contain sorbitol or sorbitane in the shell.
Figure 3:
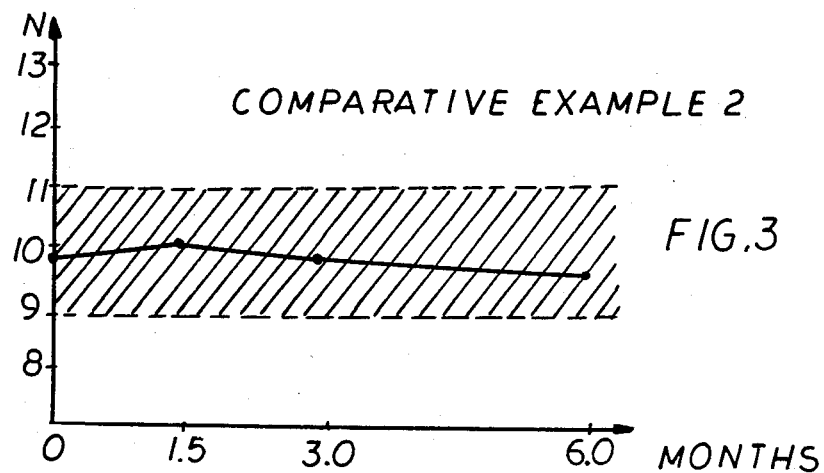
FIG. 3 is the Comparative Example 2 illustrating a decrease in capsule hardness (N) after storage where capsules contain polyethylene glycol 400 in the filling and sorbitol and sorbitane in the shell.

A very essential aspect of the present invention is to be seen in the selection of the proper polyethylene glycol. It was found that the desired properties are achieved only when at least 50% by weight of the polyethylene glycol used is a polyethylene glycol with a mean molecular weight of 600. An exceptionally satisfactory reproducibility is obtained by the exlusive use of polyethylene glycol with a mean molecular weight of 600. A polyethylene glycol of this molecular weight is, as regards its properties, at the boundary between liquid and solid polyethylene glycols and is commercially available under different trade names.

It is further of importance for the solution of the underlying problem that the filling of the capsule must contain up to 20% by weight of glycerol and/or 1,2-propylene glycol. The best reproducibility is obtained when the quantity of glycerol contained in the filling of the capsule is between 5 and 10% by weight.

Usually, the proportion of the active substance contained in the filling is between 1 and 7% by weight, but other proportions may be selected as desired.

As a rule, the filling of the dried soft gelatin capsules will still contain a certain proportion of water which may range between 4 and 20% by weight. Normally, the proportion of water will be in the range of 6 to 10% by weight, mostly 7 or 8% by weight. This proportion of water is introduced into the filling during drying of the aqueous gelatin capsules, as a result of the affinity of the filling to water.

It is of utmost importance for the present invention that the softener of the gelatin used for the shell must at least partly contain sorbitol and sorbitanes in quantities ensuring that after drying of the capsule the proportion of sorbite and sorbitanes in the dried shell will be between 4 and 40% by weight. Apart from the sorbitol and/or sorbitanes, an additional proportion of glycerol may be used as softener. However, the problem underlying the invention cannot be solved by the use of a gelatin, the softener of which consists exclusively of glycerol. Exceptionally good and reproducible results are obtained when the proportion of sorbitol and/or sorbitanes is in the range of 8 to 30% by weight, in particular in the range of 10 to 25% by weight. Sorbitanes are sorbitol anhydrides produced from sorbite by intramolecular separation of water.

Mixtures of sorbitol and sorbitanes are also commercially available under different trade names. These mixtures may, due to their particular production processes, contain small quantities of mannitol, isosorbide or other polyols in addition to the sorbitol and sorbitanes. Such mixtures of sorbitol and sorbitanes are well suited as softeners for the shell of the capsule on the condition that their sorbitol and sorbitane content is within the range specified before. The shell may contain still other usual accessory substances, such as preservatives, for instance p-amino benzoic ester and potassium sorbate, or coloring substances and pigments.

It was not forseeable, for a man of the art, that the average molecular weight of the polyethylene glycol has such a great influence on the physical stability of soft gelatin capsules, in particular as regards the capability of polyethylene glycols to diffuse through the gelatin enclosure while the latter remains intact. As will appear from the comparative tests that will be described hereafter, polyethylene glycol 400—the substance which in German Patent Specification No. 22 09 526 has been highlighted as being particularly advantageous—is in effect not suited as a filling material for the production of soft gelatin capsules which meet the high demands of the problem underlying the present invention. It is further to be regarded as surprising that the combination of the stated particular capsule filling sorbitol and/or sorbitane exhibits better properties as a softening agent than glycerol which is normally superior in this respect. Further, it could not be foreseen that, by exchanging the usually employed softener glycerol in the sorbitol partly or completely by sorbitol and/or sorbitane, it would become possible to maintain the desired adjusted hardness of the capsule during storage.

The soft gelatin capsules made up according to the invention distinguish themselves further by the fact that, due to the optimum matching of the filling and the capsule material, practically no influence of the different active substances in the filling can be noticed. The soft capsules of the invention may therefore be employed for the most different medicinal substances which can be dissolved or suspended in polyethylene glycols and which provide particular biopharmaceutical advantages when administered in combination with polyethylene glycols, in particular as regarding the release of the active substances. Capsules of excellent physical stability have been obtained, for instance, with the medicinal substances Diazepam, Indometacin and Dipyridamol.

In cases where the active substance is not dissolved, but rather is suspended in the filling which contains the polyethylene glycol, the suspension may be protected against undesirable sedimentation of the active substance during the production process by increasing the viscosity of the filling with the aid of solid polyethylene glycols. The addition of up to 20% by weight of polyethylene glycols of a mean molecular weight above 600 has no negative influence whatever on the physical stability of the capsules produced in this manner.

Apart from the fact that the filling and capsule materials must be selected in accordance with the invention, the soft gelatin capsules of the invention can be produced in the usual manner, for instance using the known R. P. Scherer method. As is generally known, the production of soft gelatin capsules comprises a first operation by which a wet capsule is formed which is thereafter dried. Accordingly, the gelatin used for making the shell of the capsule contains at the time of manufacture a considerable proportion of water which may for instance be in the range of 30 to 40% by weight. The filling material in contrast may be absolutely free from water. During drying of the capsules the water contained in the wall of the wet capsule normally does not completely vaporize. Rather, a small proportion will normally also pass into the filling. According to the present invention, such water content of the filling does not negatively influence the stability and durability of the capsule. While the method of manufacture of the soft gelatin capsules of the invention conforms otherwise to the method usually employed, one factor is really important in the method of the invention, namely that the content of sorbitol and sorbitanes must be within the specified range after drying. The water content of the gelatin used for the production of the capsule must therefore be taken into account.

The invention will now be described in detail with reference to one example of the invention and two comparative examples.

EXAMPLES

For the purpose of the example and the comparative examples, soft gelatin capsules of the specified compositions were produced under identical conditions and then stored, for the durability test, in moisture-tight glass bottles at 20° C. The physical stability was checked by means of the following two measuring methods:

1. Determination of the content of polyethylene glycols diffused into the shell: The capsule selected for investigation was cut open at the end of the storage time, and the filling which contained the polyethylene glycols was washed out using an organic solvent. Thereafter, the shell was dissolved, the polyethylene glycols contained therein were silylized and finally quantitatively analyzed by gas-chromatography.
2. Determination of the hardness of the capsule. The hardness of the capsule was measured using a commercially available hardness tester in which the capsule under examination is compressed within 20 seconds by 2 mm between a measuring detector and a plate moving slowly upwards. The counter-force exerted by the capsule is displayed in Newton by the indicating device. Under these test conditions, hardness values above 11N are indicative of an insufficient flexibility of the capsules, which values below 9N are obtained for capsules which are excessively soft.

EXAMPLE (according to the invention)

Using a usual machine for the production of soft gelatin capsules, wet capsules were produced from the following base materials:
Material for the shell:

| Gelatin | 168.0 mg |
| Glycerol, 85% | 52.0 mg |
| Sorbitol and sorbitane | 43.0 mg |
| Water | 137.0 mg |
| Material of the filling: | |
| Polyethylene glycol 600 | 459.0 mg |
| Glycerol, 85% | 51.0 mg |
| Diazepam (active substance) | 5.0 mg |

The wet capsules so obtained were dried, whereafter the dry capsules showed the following composition:
Shell:

| Gelatin | 168.0 mg |
| Glycerol, 85% | 52.0 mg |
| Sorbitol and sorbitane | 43.0 mg |

Filling:

| Polyethylene glycol 600 | 459.0 mg |
| Glycerol, 85% | 51.0 mg |
| Water | 38.0 mg |
| Diazepam | 5.0 mg |

COMPARATIVE EXAMPLE 1

In the capsule examined in this example, the shell did not contain any sorbitol and/or sorbitane, while the filling material consisted of polyethylene glycol 600, the material to be selected in accordance with the invention.

Wet capsules of the following composition were produced under conditions identical to those employed in Example 1:
Material for the shell:

| Gelatin | 175.0 mg |
| Glycerol 85% | 102.0 mg |
| Water | 123.0 mg |

Material for the filling:

| Polyethylene glycol 600 | 459.0 mg |
| Glycerol, 85% | 51.0 mg |
| Diazepam | 5.0 mg |

The dried capsules showed the following composition:
Shell:

| Gelatin | 175.0 mg |
| Glycerol, 85% | 102.0 mg |

Filling:

| Polyethylene glycol 600 | 459.0 mg |

-continued

| | |
|---|---|
| Glycerol, 85% | 51.0 mg |
| Water | 35.0 mg |
| Diazepam | 5.0 mg |

COMPARATIVE EXAMPLE 2

In this comparative example, sorbitol and sorbitane were used in the cpsule as softener, in addition to glycerol, while polyethylene glycol 400 was used for the filling. The composition of the wet capsule which was produced under conditions identical to those employed in Example 1 was as follows:

Material for the shell:

| | |
|---|---|
| Gelatin | 168.0 mg |
| Glycerol, 85% | 52.0 mg |
| Sorbitol and sorbitane | 43.0 mg |
| Water | 137.0 mg |

Material for the filling:

| | |
|---|---|
| Polyethylene glycol 600 | 459.0 mg |
| Glycerol, 85% | 51.0 mg |
| Diazepam | 5.0 mg |

The dry capsules obtained from these wet capsules showed the following composition:

Shell:

| | |
|---|---|
| Gelatin | 168.0 mg |
| Glycerol, 85% | 52.0 mg |
| Sorbitol and sorbitane | 43.0 mg |

Filling:

| | |
|---|---|
| Polyethylene glycol 400 | 459.0 mg |
| Glycerol, 85% | 51.0 mg |
| Water | 43.0 mg |
| Diazepam | 5.0 mg |

Results of the Stability Tests

1. Determination of the hardness of the capsule

The capsules of the example and the two comparative examples were checked immediately after their production, and after storage for 1½, 3 and 6 months. The results of the hardness measurements are summarized in the following Table 1 and in FIG. 1.

TABLE 1

| | Capsule hardness (N) after storage for | | | |
|---|---|---|---|---|
| | 0 | 1.5 | 3.0 | 6.0 months |
| Capsules of The example | 9.8 | 10.0 | 10.0 | 10.1 |
| Comparative example 1 | 10.3 | 11.7 | 12.3 | 12.6 |
| Comparative example 2 | 9.8 | 10.0 | 9.8 | 9.5 |

The measuring values plotted in the enclosed drawing show that the capsules of the example, with polyethylene glycol 600 in the filling and sorbitol and sorbitane in the shell, did not change their optimum hardness of approx. 10N throughout the full period of 6 months.

The capsules of the comparative Example 1, which did not contain any sorbitol or sorbitanes in the shell, changed very rapidly in hardness and became brittle.

The capsules of the Comparative Example 2, the filling of which contained polyethylene glycol 400 instead of the polyethylene glycol 600, became a little softer at the end of 3 or 6 months. This softening of the capsules indicates that the content of softener in the shell increased during the storage time, an indication which is confirmed by the following test results relating to the polyethylene glycol content in the shell.

2. Determination of the content of polyethylene glycols diffused into the enclosure At the end of the storage period of 3 and 6 months, the capsules of the example and the Comparative Example 2 were investigated to determine the polyethylene glycol content in the shell. The investigation results are summarized in Table 2.

TABLE 2

| | Capsules of Polyethylene glycol content in the shell after a storage period of | |
|---|---|---|
| | 3.0 | 6.0 months |
| Example | 1.7 mg | 3.6 mg |
| Comparative Example 2 | 9.5 mg | 13.5 mg |

The measuring values show that in the case of the capsules of the example only a very small quantity of polyethylene glycol 600 diffuses into the shell, while in the case of the capsules of comparative Example 2 a considerably greater quantity of polyethylene glycol 400 diffuses into the shell during the same period of time.

It results from the example and the two comparative examples that capsules having the desired excellent properties are obtained only if both the softener and the specific polyethylene glycol are simultaneously and properly selected. In this connection it must be noted that the comparative examples were carried out already with a view to the teachings of the present invention and that the prior art does not even contain any concrete indications that would point to the advantages connected with the use of polyethylene glycol 600 or of sorbitol and/or sorbitanes as softeners in such soft gelatin capsules. Random tests carried out with other polyethylene glycols and capsules which contained only glycerols as softener yielded even more favorable results than the comparative tests.

Accordingly, the present invention enables soft gelatin capsules of excellent stability and durability to be produced from components the use of which has been known as such, though partly in other contexts, but which have never before been combined in the specified form.

What is claimed is:

1. A soft gelatin capsule comprising a shell of gelatin and a softener, and a filling consisting of a polyethylene glycol and a low polyhydric alcohol and at least one active substance, characterized in that
   (a) the dried shell of the capsule contains 4 to 40% by weight of a mixture of sorbitol and at least one sorbitane,
   (b) at least 50% by weight of the polyethylene glycol used in the filling for dissolving or suspending the active substance is a polyethylene glycol having a mean molecular weight of 600, and (c) the capsule filling comprises up to 20% by weight of glycerol and/or 1,2-propylene glycol.

2. A soft gelatin capsule in accordance with claim 1, characterized in that the capsule filling of the dried capsule contains additionally between 4 and 20% by weight of water.

3. A soft gelatin capsule in accordance with claim 1, characterized in that the polyethylene glycol of the capsule filling consists exclusively of polyethylene glycol having a mean molecular weight of 600.

4. A soft gelatin capsule in accordance with claim 1, characterized in that the polyethylene glycol used in the capsule filling, a portion of at least 80% by weight is a polyethylene glycol having a mean molecular weight of 600 and a portion of up to 20% by weight is a polyethylene glycol having a mean molecular weight of above 600.

5. A method for producing a soft gelatin capsule in accordance with claim 1, characterized by the steps of conventionally enclosing a capsule filling made up of an active substance, a polyethylene glycol containing at least 50% by weight of a polyethylene glycol having a mean molecular weight of 600 and up to 20% by weight of glycerol and/or 1,2-propylene glycol, in an aqueous gelatin shell containing a mixture of sorbitol and at least one sorbitane and drying the capsule so obtained so that the dried capsule shell contains 4 to 40% by weight of the mixture of sorbitol and at least one sorbitane.

* * * * *